United States Patent
Nosrati et al.

(10) Patent No.: US 8,433,399 B1
(45) Date of Patent: Apr. 30, 2013

(54) METHOD AND APPARATUS FOR AN INTERACTIVELY PROGRAMMABLE ECG DEVICE WITH WIRELESS COMMUNICATION INTERFACE TO REMOTE COMPUTING DEVICES

(76) Inventors: Farhad David Nosrati, Encino, CA (US); Sandu Buraga, Lasi (RO)

(*) Notice: Subject to any disclaimer, the term of this patent is extended or adjusted under 35 U.S.C. 154(b) by 5 days.

(21) Appl. No.: 13/342,918

(22) Filed: Jan. 3, 2012

(51) Int. Cl.
*A61B 5/04* (2006.01)

(52) U.S. Cl.
USPC ............................................. 600/523

(58) Field of Classification Search ............ 600/523
See application file for complete search history.

(56) References Cited

U.S. PATENT DOCUMENTS

| | | | |
|---|---|---|---|
| 3,215,136 A | 11/1965 | Holter et al. | |
| 5,007,431 A * | 4/1991 | Donehoo, III | 600/509 |
| 6,944,495 B2 * | 9/2005 | MacAdam et al. | 600/521 |
| 6,970,737 B1 | 11/2005 | Brodnick et al. | |
| 6,987,965 B2 | 1/2006 | Ng et al. | |
| 7,136,703 B1 | 11/2006 | Cappa et al. | |
| 7,197,357 B2 | 3/2007 | Istvan et al. | |
| 7,272,428 B2 | 9/2007 | Hopman et al. | |
| 7,933,642 B2 | 4/2011 | Istvan et al. | |

OTHER PUBLICATIONS

Oswald, Alison. 'At the Heart of the Invention: Development of the Holter Monitor'. In Smithsonian Collections Blog [online]. Archives Center, National Museum of American History, Oct. 30, 2011; 8:00 am [retrieved from the Internet:<http://si-siris.blogspot.com/2011/10/at-heart-of-invention-development-of.html>.

* cited by examiner

*Primary Examiner* — George Manuel

(57) ABSTRACT

A wireless, battery-powered electrocardiograph (ECG) monitoring system, along with a method of use for detecting and analyzing patient's cardiovascular activity and interactively transmitting the data to a wireless computing device via telemetry. The wireless computing device can include but is not limited to a mobile phone, Tablet-PC or a laptop computer. ECG monitor contains a processor that continuously processes received ECG signals, stores the signals in memory and performs a series of analysis on the recorded data using pre-stored software algorithms. When an abnormality is detected, a wireless transceiver transmits the processed ECG data to a wireless computing device for viewing and further analysis, by displaying the received ECG data for doctor's viewing, sending the data to a web-based server computer for remote access, performing additional advanced analysis on the data and downloading new algorithms and instructions into the ECG monitoring device via telemetry.

20 Claims, 15 Drawing Sheets

PORTABLE WIRELESS ECG DEVICE
HARDWARE ARCHITECTURE
100

PORTABLE WIRELESS ECG DEVICE
HARDWARE ARCHITECTURE
100

PORTABLE WIRELESS ECG DEVICE
HARDWARE FLOW CONTROL
200

PROGRAMMABLE
CIRCULAR SLIDING REPORTING WINDOW (CSRW)
CONSTRUCTION PROCESS

260

METHOD AND APPARATUS FOR AN INTERACTIVELY PROGRAMMABLE ECG DEVICE WITH WIRELESS COMMUNICATION INTERFACE TO REMOTE COMPUTING DEVICES

BACKGROUND OF INVENTION

1. Field of the Invention

The present invention relates to a wireless monitoring system and, more particularly, to a wireless electrocardiograph (ECG) system, along with method of use for interactively detecting and analyzing patient's cardiovascular activity and downloading updated algorithms that are best suited for patients condition. This invention includes, but is not limited to, the continuous ECG monitoring of patients in an outpatient setting, utilizing a multi-stage analysis method and a special diagnostic reporting data buffer.

2. Description of Prior Art

ECG systems are used for monitoring activity of a patient's heart. A number of electrodes are positioned on the patient. Wires are connected from the electrodes to an ECG monitor. The ECG monitor processes the signals and outputs ECG data, in form of traces representing activity of the heart by measuring electrical signals at different positions on the patient.

Several classes of ECG monitoring devices are presently available in the market. Each of these devices exhibits major issues and limitations that the current invention resolves.

Stand-alone ECG monitoring systems are used to monitor and record patient's cardiovascular activity within a hospital or clinic and display or print the resulting waveforms for doctor's viewing. The problems associated with such devices are numerous. One fundamental problem is that the wires of these devices inhibit movement by and around the patient. Because the patient is wired to the stationary ECG device, doctors must work around the wires to gain access to the patient. Additionally, the patient cannot move freely and/or must always be accompanied by all the wires and equipment whenever the patient leaves the hospital bed. Another problem with these devices is that the wires will stress the electrodes connecting the patient to the stand-alone ECG device, resulting in malfunction or disconnection between the patient and the ECG device. Additionally, such stand-alone ECG devices are not suited for outpatient and post care applications. The devices are large and bulky and are not portable or designed for in-home care. In addition, current stand-alone ECG devices lack the flexibility to adapt themselves automatically to each patient's cardiovascular condition by interactively uploading new algorithms and software parameters for a more effective arrhythmias and other abnormal heart conditions analysis. Such devices require manual input by the care provider and are incapable of adapting themselves on-the-fly during cardiovascular monitoring process.

There are portable ECG monitoring devices that exist in several configurations that do not connect the patient to an external stand-alone device. However, these, like their stand-alone counterparts have numerous shortcomings. Many of the prior art portable ECG monitoring devices are intended to be recording devices only. These devices record cardiovascular data over long periods of time for later viewing and analysis. Additionally, these devices are incapable of performing any type of analysis of the patient's cardiovascular condition. These devices are not interactive and are not remotely programmable. An example of such devices is the ubiquitous Holter ambulatory ECG monitor. This device is worn typically around the neck of the patient and is about the size of a tape recorder. From the bottom of the Holter monitor are several wires, generally five, that attach to electrodes that are placed about the patient's torso by sticky pads. Holter monitors continuously record a patient's ECG waveform over an extended period of time such as a 24-hour period or several weeks. These devices often contain a large storage memory for recording the patient heart waves over these long time periods. The patient carries the complete monitor and recorder. The Holter ECG devices record the cardiovascular data only; they cannot scrutinize the data, they merely save it for the primary care physician to review later. The data recorded by a Holter monitor is known and can be analyzed only after the recording period is over; therefore, if the patient experiences an abnormality, the Holter device is incapable of performing an immediate analysis or of assisting the patient by interactively communicating with a doctor. Additionally, Holter monitors lack the processing power and the necessary software algorithms to immediate analyze the ECG data.

There are also portable ECG monitors that are not worn by the patient for extended time periods. These ECG monitors are hand-held monitoring devices that monitor and record for relatively short periods of time, typically a 30-minute interval, performed several times a day. A major problem with these devices is that there is a stored history of only that which was recorded. If the patient experiences a cardiovascular abnormality there is no record of it unless the patient was coincidentally recording at that moment. Additionally, these devices are not designed for extended wear and do not have a sufficient memory to record for extended times, like days and weeks on end. Nor do these devices have the battery life to sustain the monitors for such extended time periods. These devices are capable of only a very limited and generic analysis and are not able to interactively upload/download algorithms or software commands to adapt themselves to the patient's cardiovascular monitoring needs.

Additionally, among the portable extended-wear ECG monitoring devices, there are devices that store the recorded heart information and are capable of transmitting that information wirelessly, to a local base station which relays the ECG data by phone to a diagnostic center where it can be promptly scrutinized for arrhythmias. However, this method constrains the normal daily activities of the patient, as the patient must continually stay within range of the local base station. Additionally, these devices don't perform any analysis nor are they programmable or adaptable to the patient's unique monitoring needs. Of those devices that are capable of some sort of analysis, such analysis is very limited and fixed. They cannot do any in-depth analysis and because they have fixed programs, they cannot upload or download software and algorithms that customize the detection, analysis and reporting for the patient's unique and individual needs. Another inadequacy with such wireless ECG monitoring devices is their limited processing power. These small wireless ECG monitoring devices are further restricted by being able to perform a limited number of complex computations on the captured cardiovascular data, in their analysis of the data for arrhythmias and other abnormal heart conditions. The inability to perform more analysis means that these devices take a one-size-fits-all approach to their cardiovascular analysis and detection of abnormalities. Additionally, their limited battery life poses another obstacle, since due to their small battery size and extended recording requirement, the battery life is very limited, which directly prohibit the more powerful processors from conducting complex computations over extended time periods. Also, lack of flexibility further limits the capability of such wireless ECG monitoring devices. Current wireless ECG devices are not able to adapt themselves automatically to each patient's cardiovascular condition by interactively uploading new algorithms and software parameters for a more effective cardiovascular abnormality analysis.

What is needed is an ECG device that has the capability to record the patient cardiovascular activity over extended time period such as a 24-hour period or longer in conjunction with the ability to transmit the recorded data automatically or on-demand to an outside wireless computing device. Furthermore, there is a significant need for a wireless ECG monitoring device that is capable of analyzing and scrutinizing the patient's cardiovascular data for arrhythmia and other abnormal heart conditions. Also, in the event that abnormal activity or activities are detected, there is a significant need for an ECG monitor that can transmit recent history packets of the patient's cardiovascular activity prior to and including each abnormal event to a wireless computing device for doctor's viewing and further analysis. A wireless ECG device needs to also be able to adapt its internal algorithms for analyzing the recorded data to each patient's unique requirements by means of uploading additional software algorithms and computational parameters interactively from an outside wireless computing device such as a mobile phone, tablet-PC or laptop computer. Finally, because of its limited processing power and battery-life, a wireless ECG monitoring device also needs to be able to automatically tap into the superior processing power of an external computing device, thru wireless communications. The present invention provides all of the above capabilities and corrects the deficiencies of the prior art.

SUMMARY OF THE INVENTION

The present invention relates to a wireless ECG monitoring system, along with method of use for interactively detecting and analyzing patient's cardiovascular activity. The present invention ECG monitoring system includes a processor, a memory for storing processed ECG signals, and a transceiver for wirelessly transmitting ECG signal data to outside computing devices. The present invention ECG monitor also contains one or more software algorithms for detecting abnormal cardiovascular activities. The ECG processor continuously performs analysis on the recorded cardiovascular activity on real-time bases. When an abnormal event is detected, the present invention ECG device will automatically trigger an alarm and transmit wirelessly, to an outside computing device, the most recent history of patient's recorded data just prior to, and including the time during, the abnormality occurrence. Since wireless computing devices such as tablet-PCs, laptop computers, desktop computers and hospital computer networks often possess a much superior processing power and extended battery lifetime, they can then perform additional complex algorithms on the recorded data and determine which is the most suitable software algorithm and detection parameters for that particular patient. In addition, a wireless computing device can access patient's past recorded history, either on its local hard drive or on outside remote computers, to further customize the detection algorithms. The wireless computing device can then upload additional detection algorithms that are best suited for patient's condition, into the present invention ECG monitoring device wirelessly. The wireless computing device may also send command instructions to the present invention ECG device to activate a different pre-stored algorithm in the ECG monitor.

The present invention is unique and novel over the prior art in part because none of the prior art portable ECG devices are capable of interactively communicating with other computing devices. Not only can the present invention do this, but it also does this while the device records and analyzes the patient's cardiovascular activity. Additionally, the prior art capacity to scrutinize a patient's heart condition is limited to their on-board processor. The present invention resolves this obstacle. The present invention is capable of scrutinizing the patient's cardiovascular condition continuously for extended periods of time and, in the event of a detected abnormality, communicating that information to more powerful outside computers via telemetry to further analyze the information. Outside computers are equipped with larger more superior processors and can perform multiple analysis processes, and identify the best-suited algorithm for the patient's cardiovascular condition. Additionally, the present invention then downloads interactively from the outside computer, the above-mentioned best-suited algorithm, and stores it in its flash memory for future analysis of the patient's condition. This resolves a primary deficiency in the prior art.

The present invention is unique and novel because none of the prior art portable ECG devices are capable of creating a log of most recent cardiovascular activity leading to each abnormal event, referred to herein as the Sliding Reporting Window (SRW) and Circular Sliding Reporting Window (CSRW), nor can they communicate the recorded information embedded in those SRWs and CSRWs to outside computers for more in-depth analysis, both of which are a significant innovations of the present invention. The SRW and CSRW of the present invention records heart signals and allows outside computers to better isolate and scrutinize all abnormalities in patient's cardiovascular condition. One of the innovations of the present invention is the creation of a series of SRW and CSRW buffers, based on patient's heart condition, and logging the history of those SRWs and CSRWs along with Date & Time stamp, and uploading and presenting them to the outside computer for further analysis.

None of the prior art portable ECG devices posses the flexibility to dynamically program the size of the recorded information leading to each abnormal cardiovascular event. It is another innovation of the present invention that it is capable of dynamically programming the duration (size) of its SRW and CSRW buffers, both by commands received from outside computers via telemetry, as well as through buttons and switches pressed by the patient or the doctor, using its Human Interface Device module.

Another innovation of the present invention is that the present invention provides support for an outside device to actively select and activate any of the pre-loaded algorithms to scrutinize patient's cardiovascular activities. None of the prior art portable ECG devices support this capability.

It is another object of the present invention to monitor and record patient's cardiovascular activity, and further to analyze patient recorded cardiovascular activity on real-time basis, and in case of an abnormality, wirelessly transmit patient's recent recorded history, which includes data leading up to and including the abnormal event, to an outside computing device, for further complex analysis. This is preferable because outside computing devices generally have superior processing power and can more quickly determine the best-suited detection algorithm for the recorded ECG data.

It is another object of the present invention to interactively communicate with a wireless computing device to receive updated software algorithms and command instructions that are most applicable to the patient's earlier recorded history. This process of interactive wireless linking between the ECG device and outside computer enables the ECG device to automatically configure itself to the patient's cardiovascular activity.

It is an object of the present invention to provide a web-based monitoring system for all patient's recently recorded history strips, SRWs and CSRW, leading to the abnormal event. The wireless computing device receiving the recent ECG history data, will create a log of all data packets received, and transfer the recorded data packets to a remotely located server computer connected to Internet. A special website will allow doctors to access and view various packets of information pertaining to each patient.

It is another object of the present invention to communicate via telemetry with outside wireless computing device to receive software commands for setting the time duration for the patient recently recorded history SRW and CSRW leading to an abnormal activity. This recently recorded history will then be transmitted to outside computing device for further analysis via telemetry.

It is another object of the present invention to communicate via telemetry with outside wireless computing device to report the status of available memory and battery charge of the present invention ECG device.

It is another object of the present invention to allow the operator to set the length of duration for the patient recently recorded history, SRWs and CSRWs, leading to an abnormal activity, via the user interface buttons of the wireless ECG monitor.

Further novel features and other objects of the present invention will become apparent from the following detailed description and discussion.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

It should be noted that references to "an," "one," or "various" embodiments in this disclosure are not necessarily to the same embodiment, and such references contemplate more than one embodiment.

The present invention method and apparatus disclosed herein is a portable ECG device equipped with an analog sensor circuitry, one or more microprocessors, storage memory and wireless connectivity, and software algorithms for analyzing the recorded information about a person's heart condition and for providing a method of interactively, and without the patient's intervention, providing customized analysis software best suited for the patient's cardiac monitoring needs.

Disclosed herein and illustrated in FIGS. 1 through 15 is the present invention method and apparatus ECG monitor 10.

Figure 1:
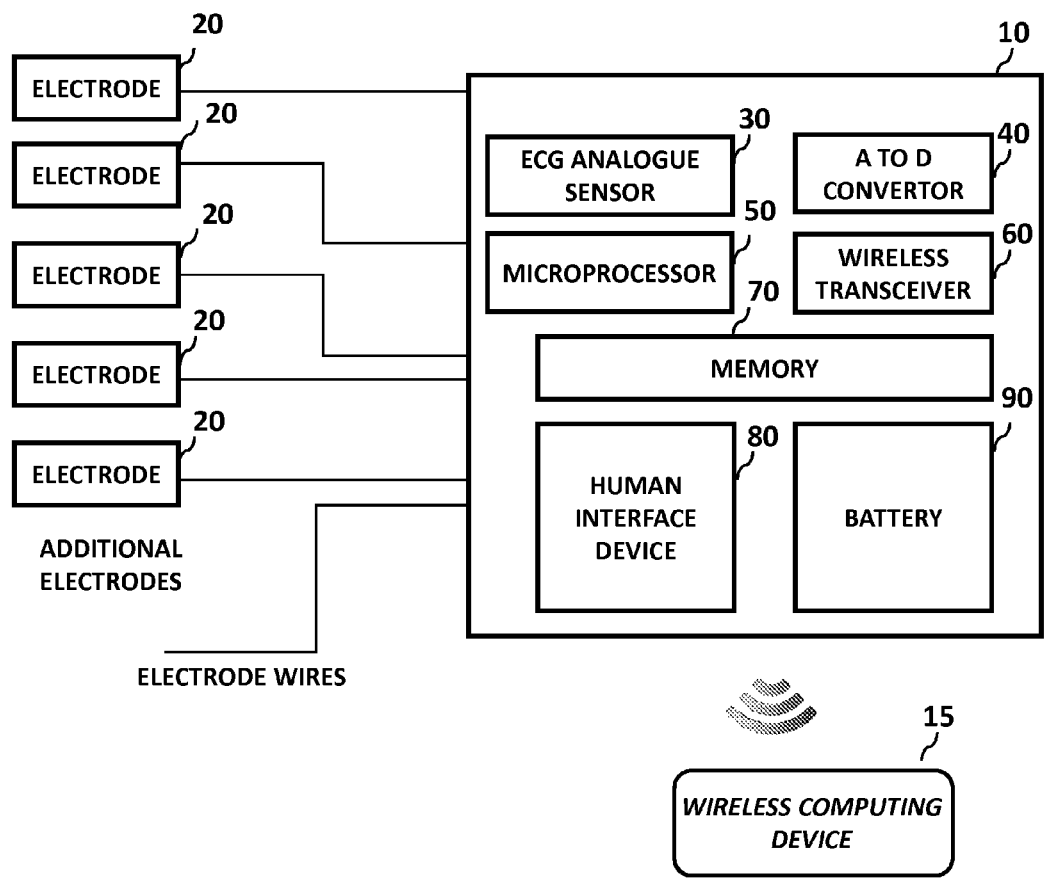
FIG. 1 is a block diagram of a preferred embodiment of the hardware architecture of the present invention Portable Wireless ECG Device.
Figure 2:
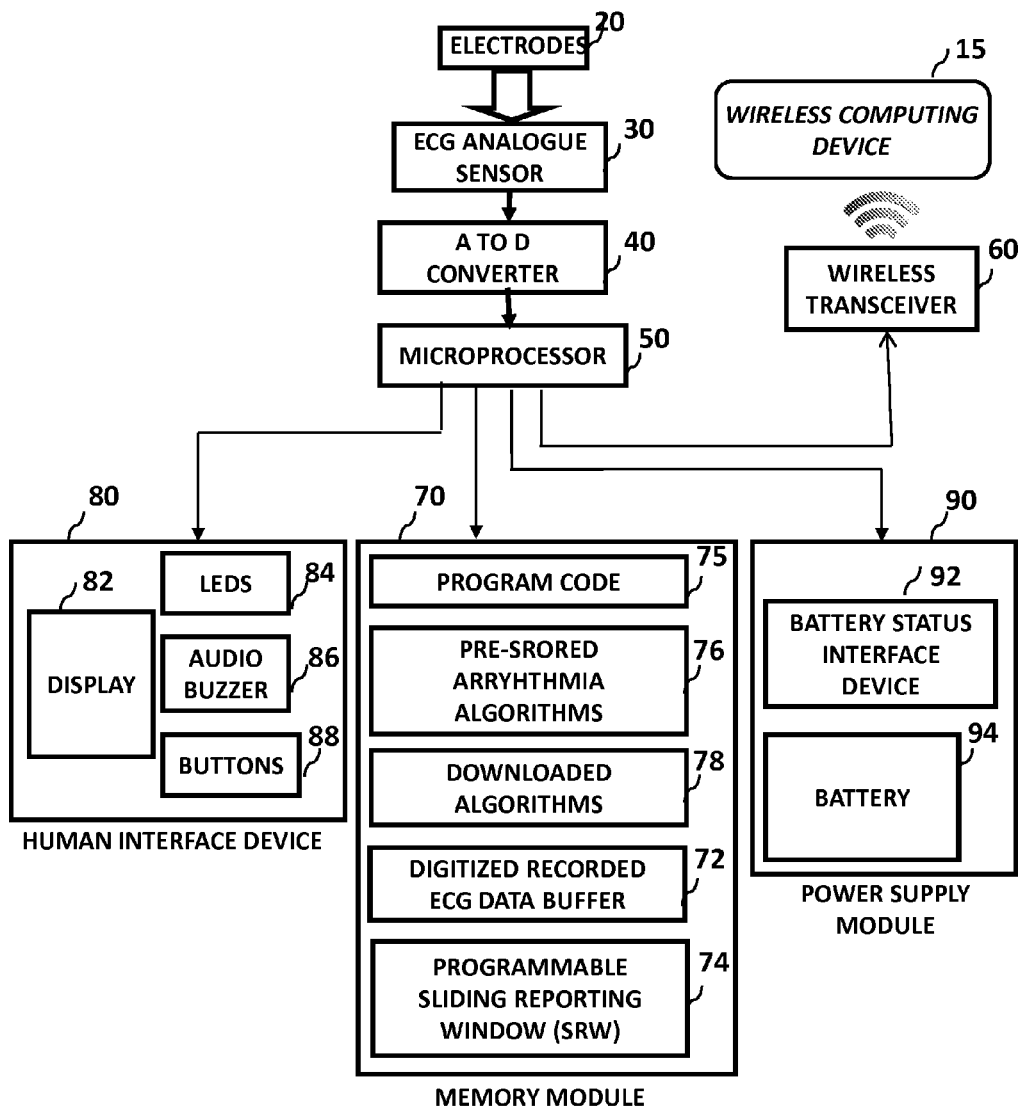
FIG. 2 is a detail illustration of the hardware architecture shown in a block diagram of a preferred embodiment illustrating the hardware flow control of the present invention Portable Wireless ECG Device.

The present invention 10 has a hardware architecture 100, which is illustrated in FIG. 1 and in detail in FIG. 2, wherein a plurality of electrodes 20 are placed on the patient's body, and are connected to the present invention 10. The hardware architecture is contained within some type of appropriate housing, not shown, the electrodes 20 connect to the hardware architecture 100 via a series of wires. The present invention 10 includes an analog sensor module 30 that receives the electrical signals from the electrodes 20 through the series of wires, and provides proper filtering and amplification circuitry to produce the desired waveform representing the patient's cardiovascular activity. The present invention includes an Analog to Digital (A to D) module 40 for digitizing the received analog waveforms. The current invention also includes a microprocessor 50 that provides the necessary computing power to process the digital data from the A to D module 40 and store the recorded information in the internal ECG data buffer 72 of the ECG memory module 70. The processor 50 also performs a series of algorithms stored in its algorithm memory 76 for detecting arrhythmia and other abnormal heart activities. A wireless transceiver 60 will communicate the recorded information to outside computing devices 15 via telemetry. User Interface module 80 of the current invention 10 includes a display unit 82 for viewing ECG waveforms as well as various prompts and messages. User interface module 80 also includes a plurality of buttons and switches 88 for manually entering various commands to program the ECG device 10 as required. An audio device 86 is available to prompt the patient of any abnormal heart activity. A number of light emitting diodes (LEDs) 84 will also provide the operator with visual feedback of the status of the current invention. A rechargeable battery 90 provides the power source for the ECG device 10, and the supporting circuitry 92 provides feedback to the status of the battery-charge available.

The present invention 10 has a hardware flow control 200, which is illustrated in FIG. 2. Electrodes 20 carry the cardiovascular signals, via connecting wires, to the ECG Analog Sensor circuitry 30. The resulting analog signals then pass through the A to D converter 40 wherein they become digitized. A microprocessor 50 accesses the digitized signals produced by the A to D converter 40.

The microprocessor 50 then saves this data in the Digitized Recorded ECG Data Buffer 72, which is located in the Memory Module 70. Also contained in the Memory Module 70 are Program Code 75, Pre-Stored Abnormality Detection Algorithms 76, Downloaded Algorithms 78, and a Programmable Sliding Reporting Window (SRW) 74. The Program Code 75 contains the main set of instructions for the microprocessor 50 to execute. The Pre-stored Abnormality Detection Algorithms 76 are the set or series of detection software algorithms that are pre-loaded on each ECG device 10 for the general purpose of detecting abnormal cardiac behavior. These algorithms are utilized for initial monitoring purposes, meaning that these are the algorithms used prior to the existence of any specific information data, pre-existing cardiovascular behavior, or patient history. These algorithms perform a broad range of general analysis of the digitized signals to determine if an abnormality may have occurred, is occurring or may be likely to occur in the near future. A key innovation of the present invention 10 is the Downloaded Algorithms 78. These algorithms are uniquely customized and downloaded, from an outside wireless computer, according to the patient's unique history, and specialized monitoring and analysis needs. In the event that an abnormality is detected, the patient's recent recorded history is saved in the SRW buffers 74, which is then transmitted to an outside computing source for further analysis to determine a customized algorithm which will then be downloaded into the ECG's 10 Downloaded Algorithm memory 78. In-depth analysis can be performed on the data in the SRW and depending on the severity of the abnormality, calls to a healthcare provider can be made to make contact with the patient, ambulances can be called, and other health related care can be performed.

Using the human interface device 80 of the current invention, the microprocessor 50 provides the means for the patient or the doctor to reprogram the ECG device 10 through a series of buttons and switches 88. In the event of the detection of an abnormality, an audio feedback 86 and visual feedback and communication is provided via the display 82 and the LED (light emitting diodes) 84.

The Power Supply Module 90 contains a battery device 94 and the supporting battery status indicator 92.

Also in communication with the microprocessor 50 are wireless transceivers 60 which transmit to the outside wireless computing device 15, patient's recorded ECG data, and also the SRW 74, as appropriate. Additionally, the transceivers 60 are used to download customized detection algorithms 78 from wireless computing devices 15 and save them in the downloaded algorithms 78 of the ECG 10.

Figure 3:
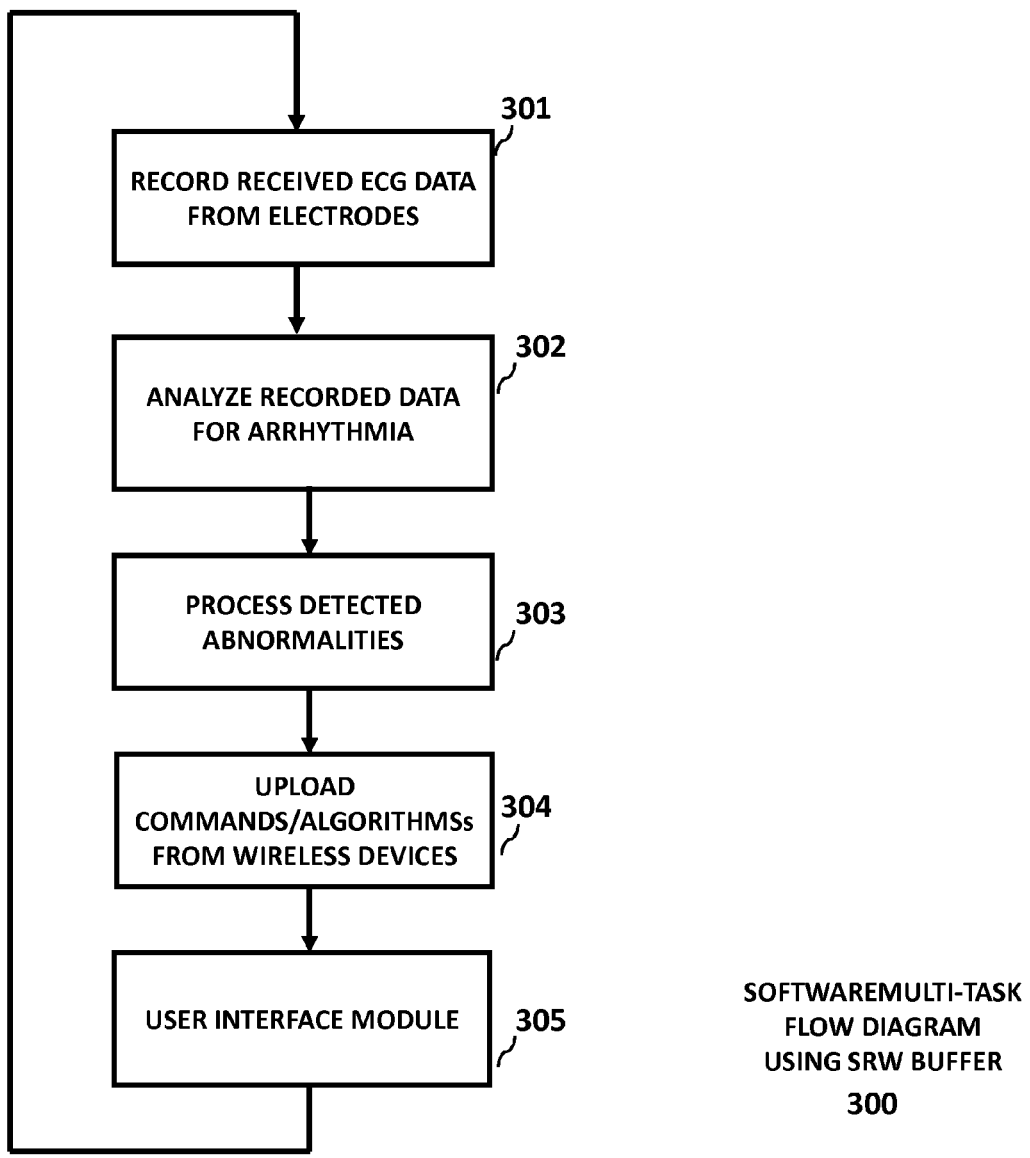
FIG. 3 is a flow chart diagram of a preferred embodiment of the software flow control of the present invention Portable Wireless ECG Device using Sliding Reporting Window (SRW) buffer.
Figure 7:
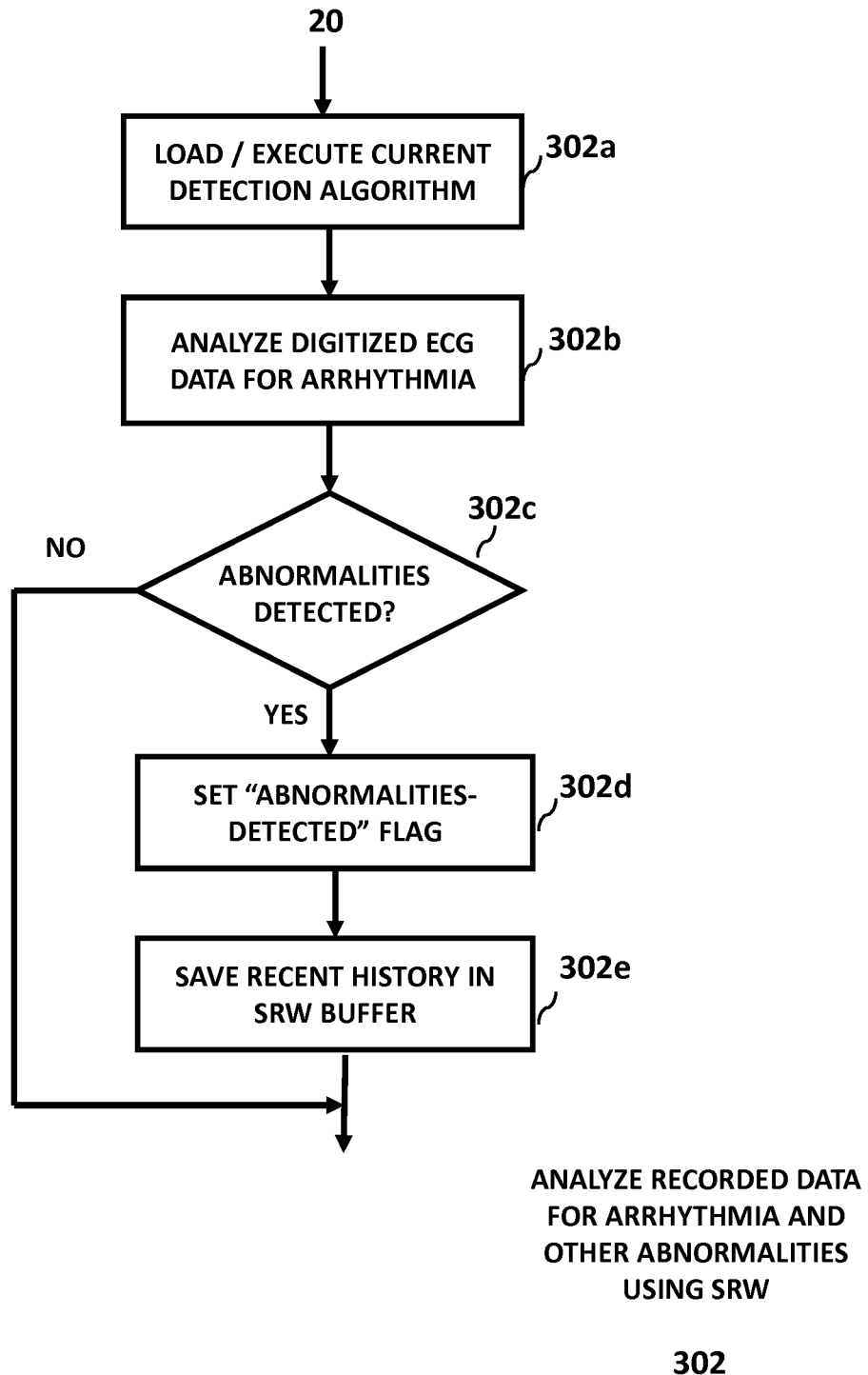
FIG. 7 is a flow chart diagram of a preferred embodiment of the analyzing of the recorded ECG Data for abnormal cardiovascular activity of the present invention Portable Wireless ECG Device using Sliding Reporting Window (SRW)
Figure 9:
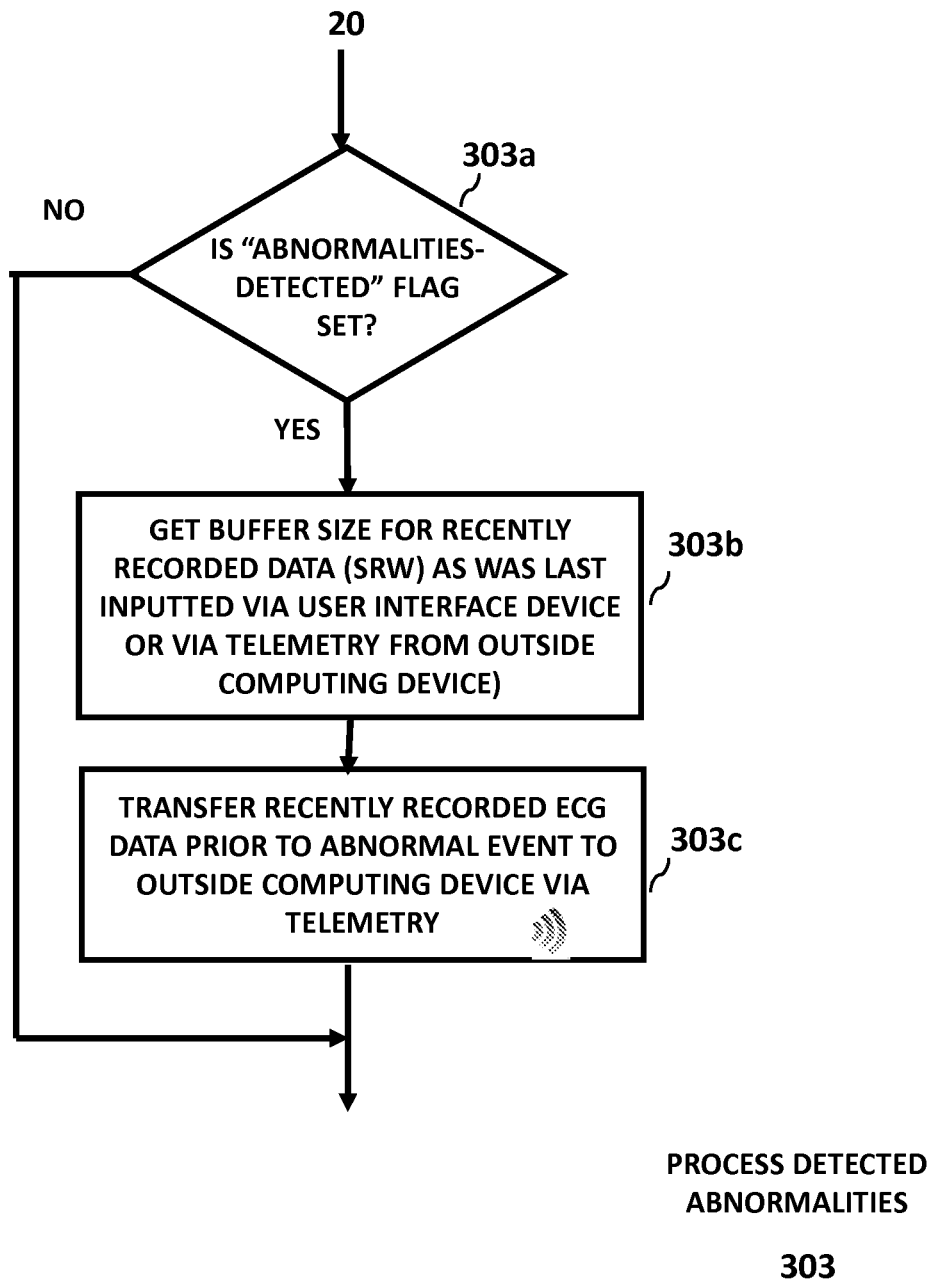
FIG. 9 is a flow chart diagram of a preferred embodiment of the process after the detection of a cardiovascular abnormality of the present invention Portable Wireless ECG Device.
Figure 10:
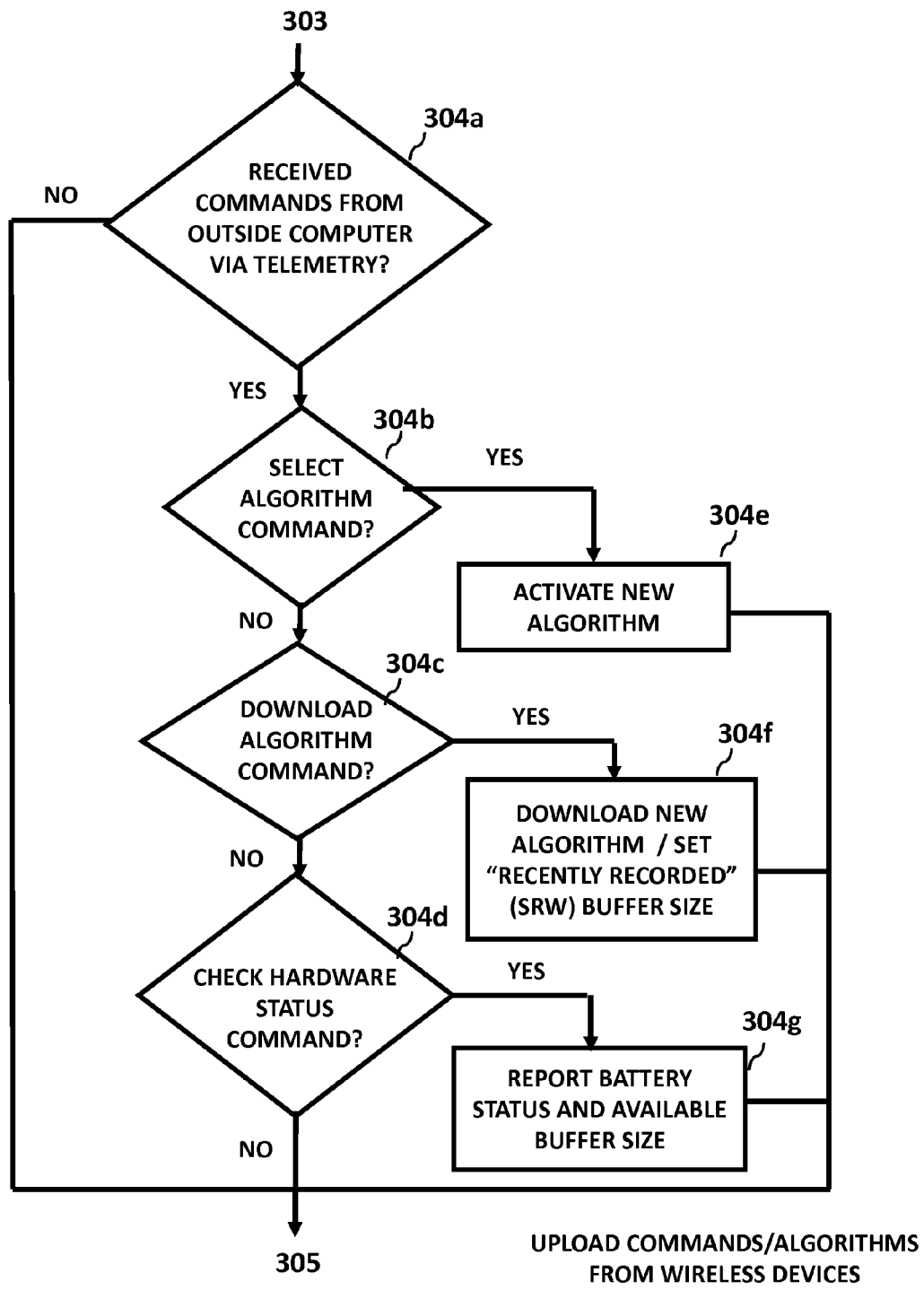
FIG. 10 is a flow chart diagram of a preferred embodiment of the customized programming, through the process of downloading software algorithms and commands from wireless devices, of the present invention Portable Wireless ECG Device.
Figure 11:
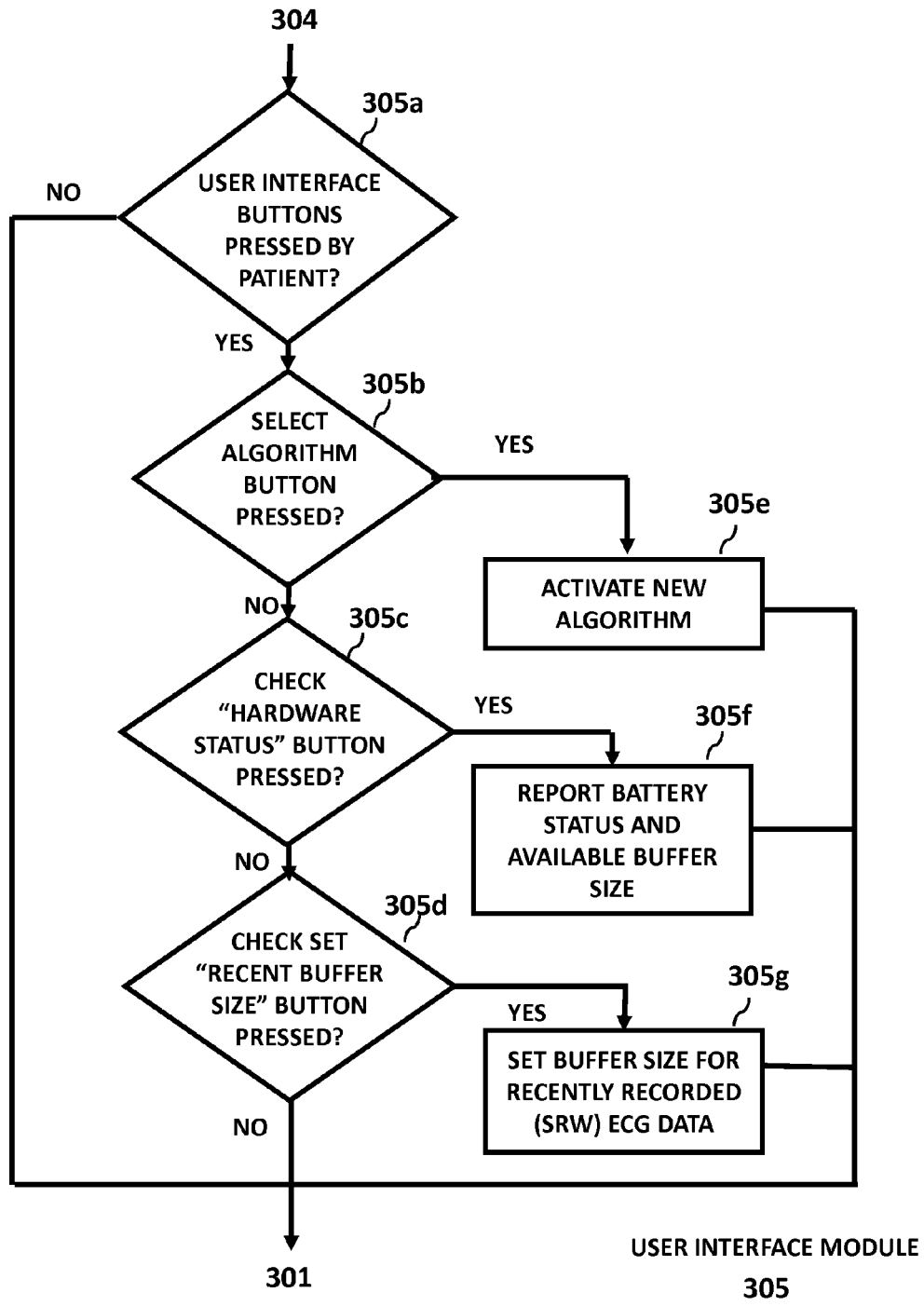
FIG. 11 is a flow chart diagram of a preferred embodiment of the User Interface Module of the present invention Portable Wireless ECG Device.

Referring now to FIG. 3, there is shown a detail of a software multi-task flow diagram 300. The initial task 301 obtains the electrical signals from the electrodes 20 and digitizes and stores the digital data in recorded ECG data buffer 72, see FIG. 5. The next task 302 scrutinizes the digitized ECG data for arrhythmia and other abnormal behavior, using pre-stored analysis algorithms, which is illustrated in FIG. 7. Next, task 303 checks the results of the algorithms that were performed and, in the event that an abnormality was detected, the patient's recent recorded history leading up to the abnormal event, the SRW, is then transmitted wirelessly to an outside computing device 15, see FIG. 1, via on-board wireless transceivers 60, which are illustrated in FIG. 9. This allows the wireless ECG device 10 to tap into the superior processing power of an outside computer 15, see FIG. 1, to further analyze and generate customized algorithms that are best suited for the patient's heart condition. Once updated algorithms are produced by outside computing devices, the next software task 304, which is illustrated in FIG. 10, manages receiving those algorithms via the wireless transceivers 60, see FIG. 1, and stores them in the internal download-algorithms memory 78 of the current invention 10. Next, the user interface task 305, which is illustrated in FIG. 11, allows manual programming of the ECG device 10, as well as providing a feedback as to the status of the ECG operation. Each of these software tasks is described in further detail below.

Figure 4:
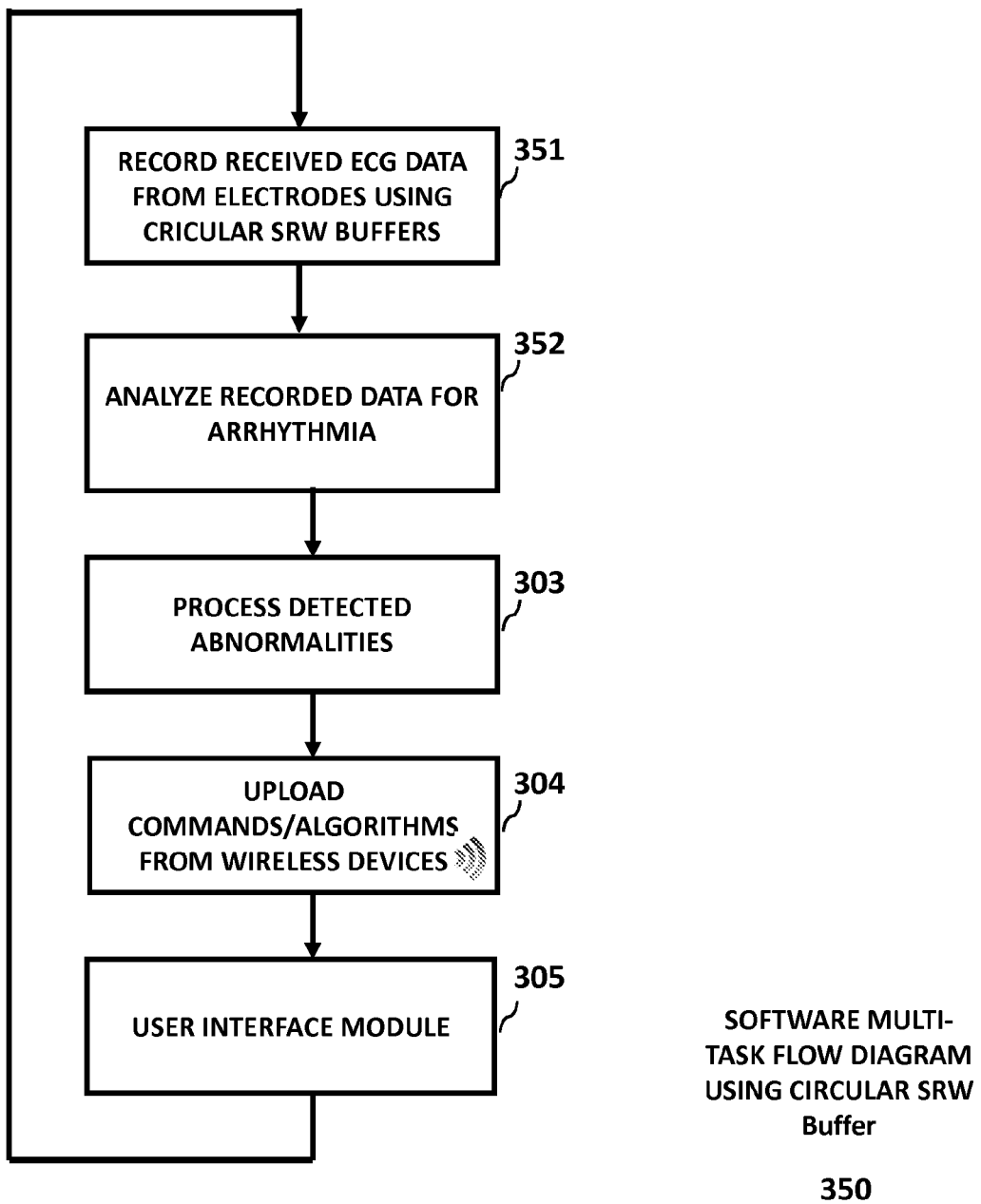
FIG. 4 is a flow chart diagram of a preferred embodiment of the software flow control of the present invention Portable Wireless ECG Device using Circular Sliding Reporting Window (CSRW)
Figure 8:
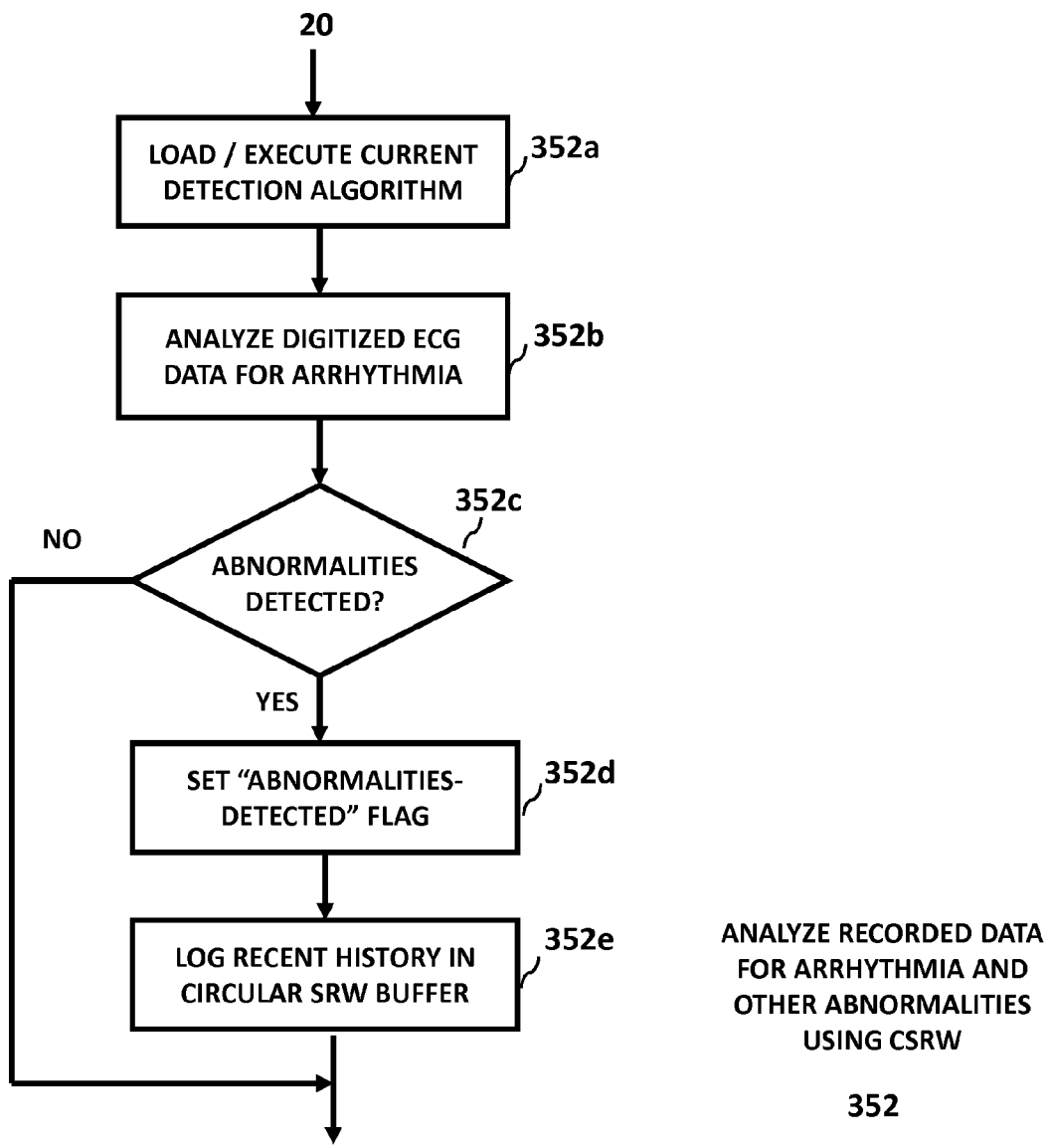
FIG. 8 is a flow chart diagram of a preferred embodiment of the analyzing of the recorded ECG Data for abnormal cardiovascular activity of the present invention Portable Wireless ECG Device using Circular Sliding Reporting Window (CSRW)

Referring now to FIG. 4, there is shown a detail of a software multi-task flow diagram using Circular SRW buffers 350 (CSRW). The initial task 351 obtains the electrical signals from the electrodes 20 and digitizes and stores the digital data in both recorded ECG data buffer 72 and in the CSRW buffers, see FIG. 6. The next task 352, which is illustrated in FIG. 8, scrutinizes the digitized ECG data for arrhythmia and other abnormal behavior, using pre-stored analysis algorithms. Next, task 303 checks the results of the algorithms that were performed, and in the event that an abnormality is detected, the patient's recent recorded history leading up to and including the abnormal event, the CSRW is then transmitted to outside wireless computing device 15, see FIG. 1, via on-board wireless transceivers 60, which are illustrated in FIG. 9. This allows the wireless ECG device 10 to tap into the superior processing power of an outside computer 15, see FIG. 1, to further analyze and generate customized algorithms that are best suited for the patient's heart condition. Once updated algorithms are produced by outside computing devices, the next software task 304 manages receiving those algorithms via the wireless transceivers 60, see FIG. 1, and stores them in the internal download-algorithms memory 78 of the current invention 10, which is illustrated in FIG. 10. Next, the user interface task 305 allows manual programming of the ECG device 10, as well as providing a feedback as to the status of the ECG operation, which is illustrated in FIG. 11. Each of these software tasks is described in further details below.

Figure 5:
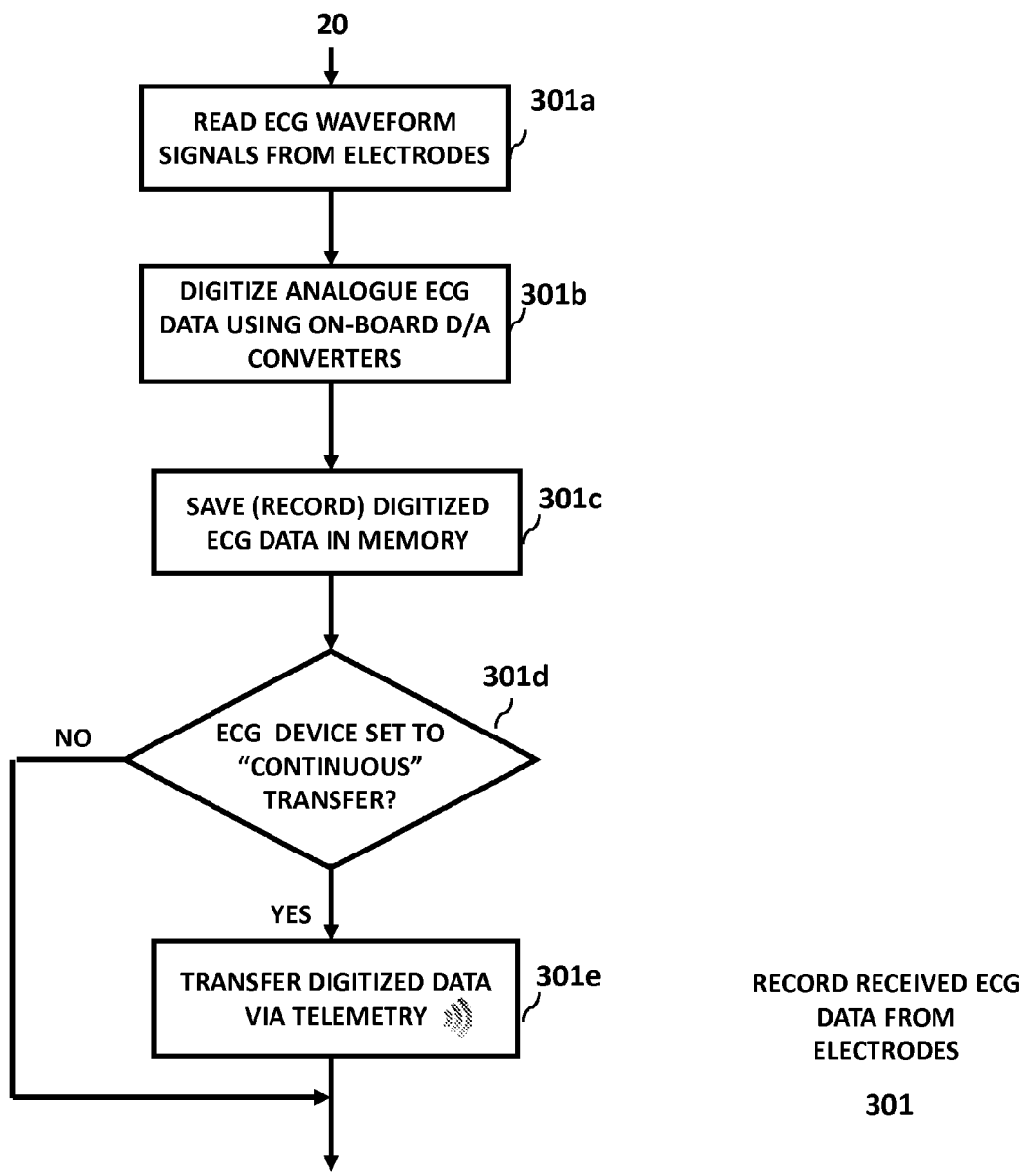
FIG. 5 is a flow chart diagram of a preferred embodiment of the recording of the received ECG Data from electrodes of the present invention Portable Wireless ECG Device using Sliding Reporting Window (SRW)

As illustrated in task diagram 301, which is recorded received ECG data 301, illustrated in FIG. 5, electrical signals are received 301a, digitized 301b and stored 301c in the ECG monitoring device's memory 70 for recorded data 72. Following that, the operation mode of the ECG is examined 301d. In the event that ECG device is set to "Continuous Transfer" mode, then the digitized signals are also transmitted 301e to outside wireless computing device 15 via on-board wireless transceivers 60.

Figure 6:
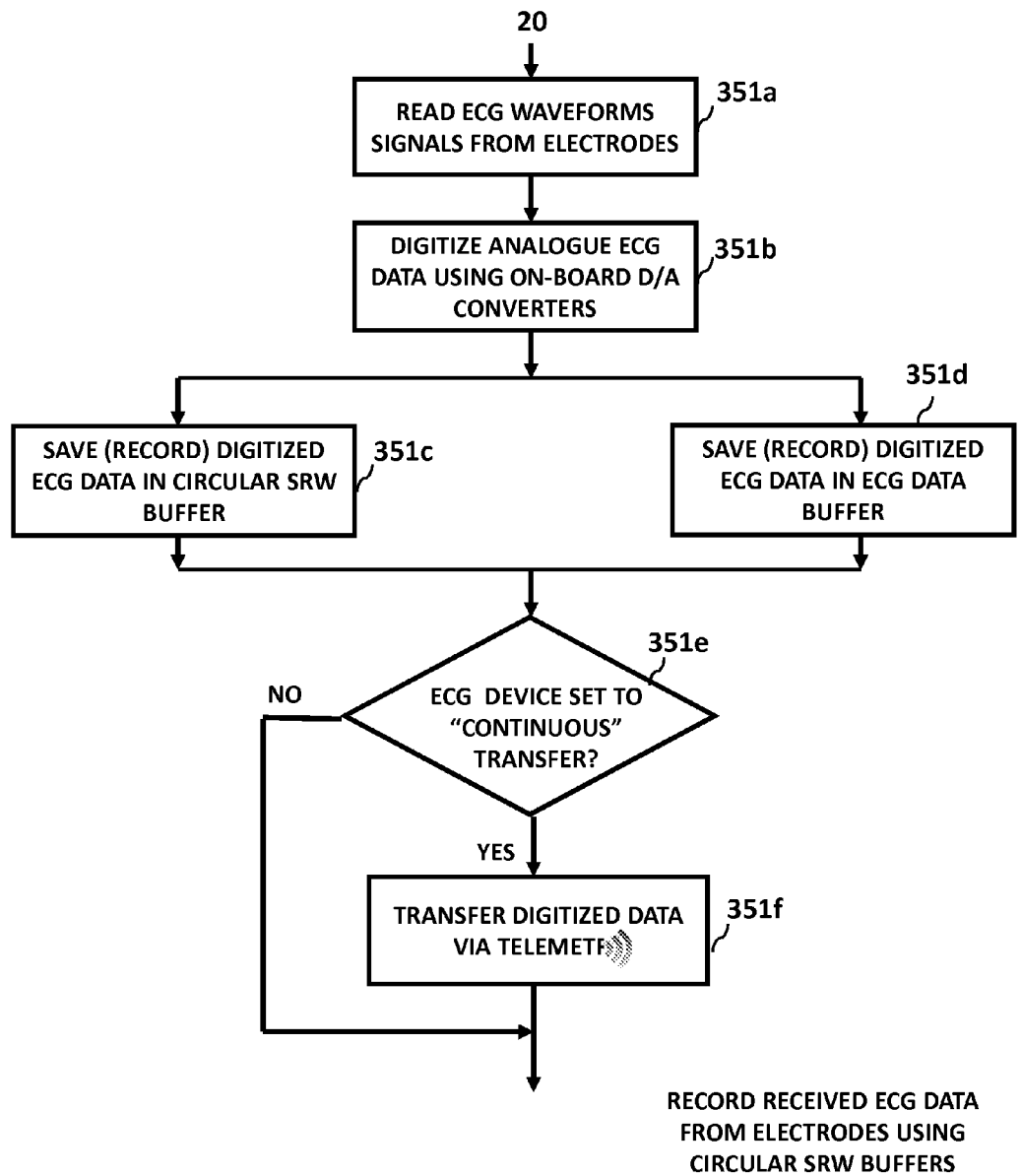
FIG. 6 is a flow chart diagram of a preferred embodiment of the analyzing of the recorded ECG Data for abnormal cardiovascular activity of the present invention Portable Wireless ECG Device using Circular Sliding Reporting Window (CSRW)

As illustrated in FIG. 6, recorded received ECG data using CSRW buffers 351 task diagram, electrical signals are received 351a, digitized 351b and stored in the CSRW buffer 351c and the recorded ECG data buffer 351d in the ECG monitoring device's memory 70, after which the operation mode of the ECG device is examined 351e. In the event that ECG device is set to "Continuous Transfer" mode, then the digitized signals are also transmitted 351f wirelessly to an outside computing device 15 via on-board transceivers 60.

As illustrated in FIG. 7, the Analyze Recorded Data task diagram 302, is shown in detail and is the software task for analyzing the recorded data for arrhythmia and other cardiovascular abnormalities. ECG monitor 10 contains a number of pre-loaded software algorithms for scrutinizing 302a patient's ECG signals for abnormalities in its recorded ECG data buffer memory 72. In addition, the ECG device 10 can download and store additional software algorithms 302a from outside computing devices 15 via its wireless transceivers 60 and save those algorithms in the downloaded-memory buffer 78 of the ECG device 10. The most recently selected algorithm is then continuously performed on the recorded ECG data as shown in 302b. In the event that abnormal cardiovascular activity is detected 302c, a software "abnormalities detected" flag is then set 302d. The recently recorded ECG data prior to the abnormal event is then saved in the SRW 302e.

As illustrated in FIG. 8, the analyze recorded data using a CSRW buffer task diagram 352, is shown in detail and is the software task for analyzing the recorded data for arrhythmia and other cardiovascular abnormalities. ECG monitor 10 contains a number of pre-loaded software algorithms for scrutinizing 352a patient's ECG signals for abnormalities in the recorded ECG data buffer memory 72. In addition, the ECG device 10 can download and store additional software algorithms 352a from outside computing devices 15 via wireless transceivers 60 and save those algorithms in the downloaded memory buffer 78 of the ECG device 10. The most recently selected algorithm is then continuously performed on the recorded ECG data as shown in 352b. In the event that abnormal cardiovascular activity is detected 352c, a software "abnormalities detected" flag is then set 352d. The current CSRW is then logged for further analysis by outside computing devices 302e.

As illustrated in the Process Detected Abnormalities task diagram 303, which is illustrated in FIG. 9, there is shown the software task that checks the status of the above mentioned "abnormalities-detected" software flag 303a, and in the event this flag is set, then the size of the recently recorded ECG data leading to the abnormal event 303b which is stored in the SRW buffer 74 is sent 303c to an outside mobile device 15 via wireless transceivers 60. The size as determined by 303b, of the SRW 74 buffers, which represents the amount of data prior to the abnormal event being transferred, is programmable via the outside wireless device 15 as well as via the user interface device module 80 of the ECG device 10. In other words, the size is both the length of time that is recorded and also the size of the memory space required to store this data. The larger memory space available, the longer the period of time that can be recorded.

As illustrated in the Upload Commands & Algorithms task diagram 304, which is illustrated in FIG. 10, there is shown the software task that manages uploading of new algorithms and commands 304a sent from outside wireless devices 15 into the ECG monitor device 10 via wireless transceivers 60. Select Algorithm Command 304b selects one of the stored detection algorithms 304e in the ECG device 10. Download Algorithm Command 304c can download and store customized detection algorithms to detect arrhythmia and other abnormal cardiovascular activities 304f into the downloaded algorithm memory 78 in the ECG device 10 from outside computing devices 15 via wireless transceivers 60. Additional software commands can be downloaded that are then used to reprogram the ECG monitoring device 10. One such command sets the size of the SRW 74 for the recently recorded history 304f of the ECG data prior to an abnormal event. In case of an abnormality, the data stored in the SRW buffer 74 will be transmitted 303c to the outside computing device 15 for further analysis. Another command can be used to activate one of the pre-loaded algorithms for detecting abnormalities 304f. Yet another command can request the status of available memory 304g or battery size 304g from the ECG device 10.

As illustrated in the User Interface Module task diagram 305, which is illustrated in FIG. 11, there is shown the software task that manages utilization of a series of buttons and switches 88 along with the display unit 82 of the User Interface Module 80 to reprogram the ECG monitoring device 10. Among features that can be programmed through these buttons 305d, is the size of the SRW buffers 74 as shown in task 305g. Additional buttons 305b can activate one of the algorithms 305e in the pre-stored algorithm buffer 76 and the newly downloaded algorithm from downloaded algorithm buffer 78. Additional buttons 305c, check the status of available recorded ECG data buffer size 72 and battery 94 condition 305f from the ECG device 10.

Figure 12:
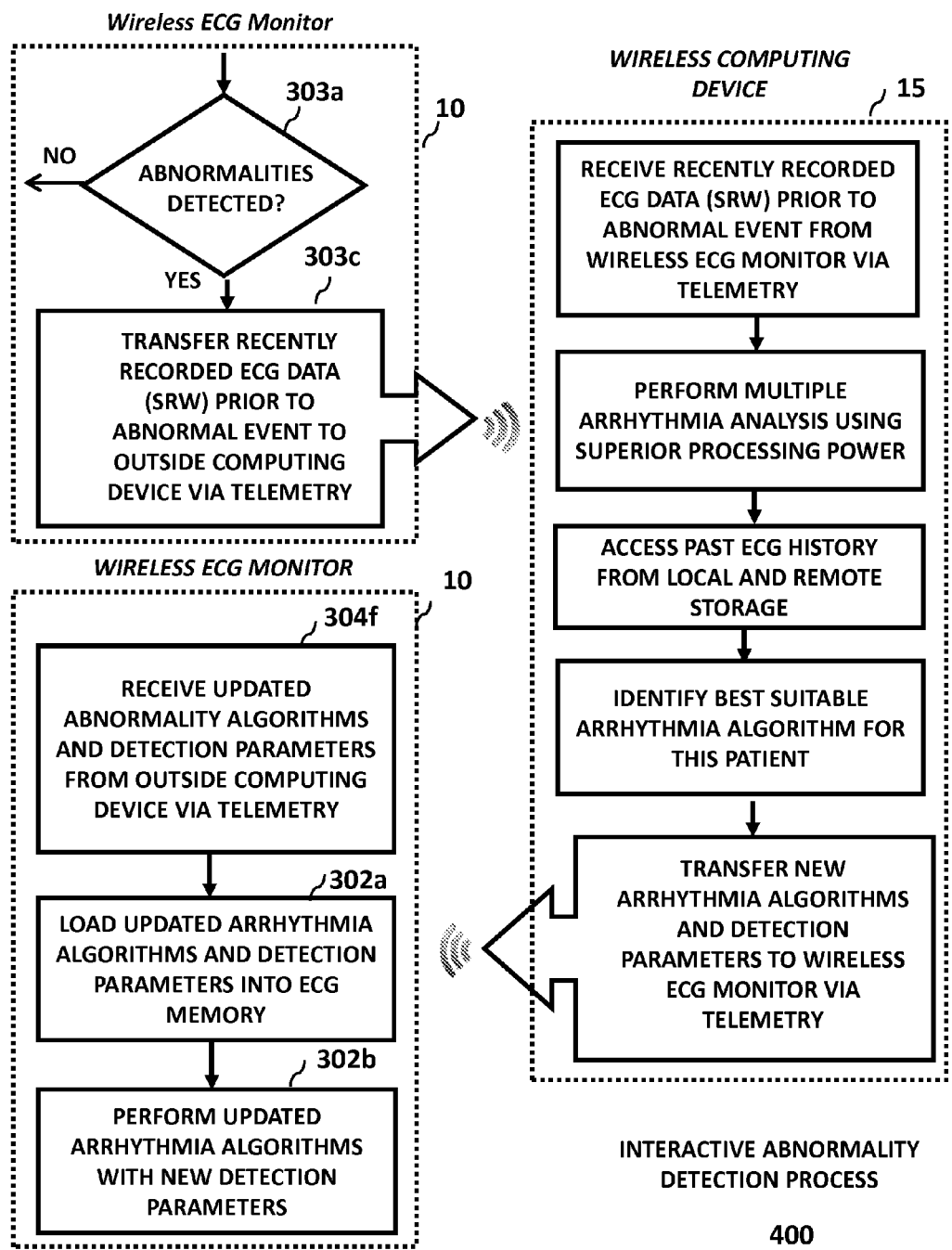
FIG. 12 is a process diagram of a preferred embodiment of the Interactive Cardiovascular Abnormality Detection Process of the present invention Portable Wireless ECG Device.

As illustrated in the Interactive Abnormality Detection Process diagram 400, which is illustrated in FIG. 12, there is shown the interactive process to detect arrhythmia and other cardiovascular abnormalities 302 using the wireless ECG monitoring device 10. ECG device 10 uses an on-board microprocessor 50 to continuously analyze recorded ECG data for arrhythmia and other abnormalities. In the event that an abnormal event is detected 303, the ECG device 10 wirelessly transmits the SRW buffer 74, which is the recent history of patient's recorded data leading to and including the abnormality, the size of which has been previously determined, to an outside computing device 15 for further analysis via wireless transceivers 60. The outside computing device 15 then uses its superior processing power, as well as its access to the patient's historical data, to generate additional software algorithms that are best fit for that patient. The new algorithms are then downloaded 304f to the ECG device 10 and saved in its internal Downloaded-Algorithm memory 78 via telemetry using the wireless transceivers 60 of the ECG device 10.

Figure 13:
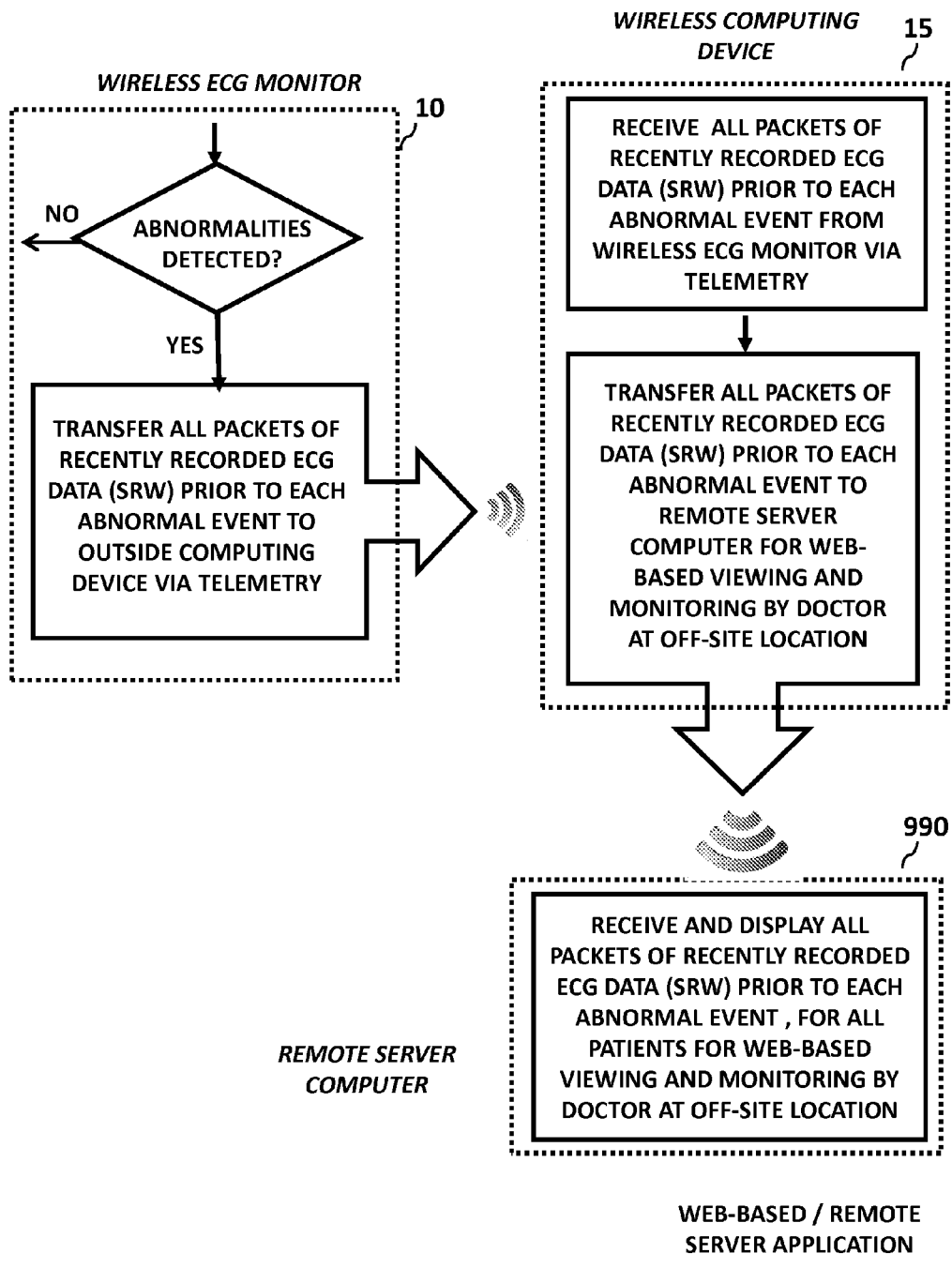
FIG. 13 is a process diagram of a preferred embodiment of the Web-based/Remote Server Application of the present invention Portable Wireless ECG Device.

As illustrated in the Web-based/Remote Server application process diagram 500, which is illustrated in FIG. 13, there is shown the ECG device 10 process for transferring the stored data in its CSRW or SRW buffers 74 to the outside computing device 15 using the wireless transceiver 60 via telemetry. The outside computing device 15 will then send the recorded packets to a remotely located server computer 990, which is connected to the Internet. A special website will allow doctors to access various packets of SRW buffered data 74 pertaining to each patient.

Figure 14:
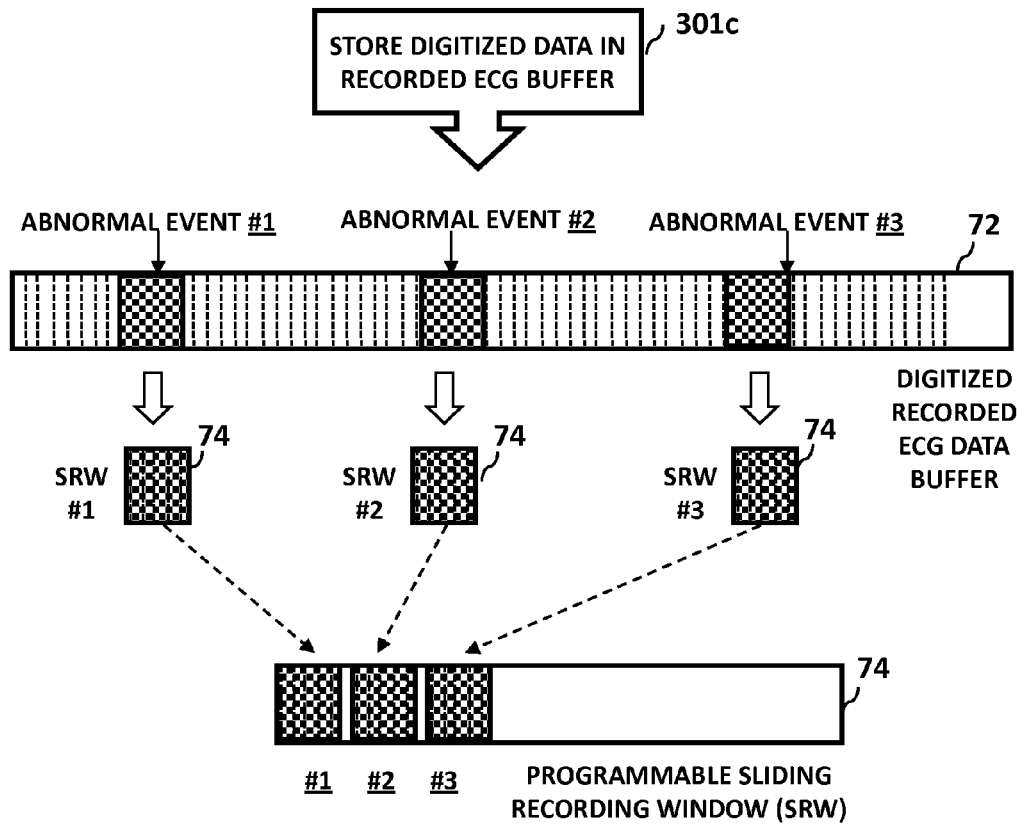
FIG. 14 is a process diagram of a preferred embodiment of the Programmable Sliding Reporting Window (SRW) Construction Process of the present invention Portable Wireless ECG Device.

A key innovation of the present invention is the programmable SRW construction 250 of the buffer 74. As illustrated in FIG. 14, there is shown the Construction Process for the Programmable SRW 74 of the wireless ECG monitoring device 10. In the event that one or more abnormal event is detected 303a, the ECG device saves the recent history of patient's recorded data prior to and leading up to each abnormality 302d, along with its proper logging information and Time & Data stamp in the SRW buffer 74 in the memory module 70 of the wireless ECG monitoring device. The SRW buffers 74 will then be transmitted to a computing device 15 via the wireless transceivers 60 for further analysis. The outside computing device 15 can then utilize its superior processing power as well as its access to the patient's historical data, to generate additional software algorithms that are best fit for that patient. The new algorithms are then downloaded to the ECG device 10 and saved in its downloaded algorithm memory 78 using wireless transceivers 60 via telemetry.

Figure 15:
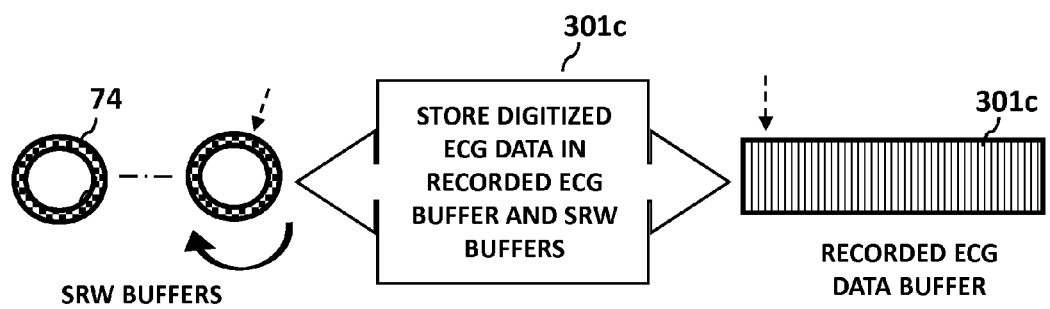
FIG. 15 is a process diagram of a preferred embodiment of the Programmable Circular Sliding Reporting Window (CSRW) Construction Process of the present invention Portable Wireless ECG Device.

Another key innovation of present invention is the construction of a programmable Circular Sliding Reporting Window, CSRW of buffer 74, which is an alternative to the SRW construction for buffer 74. As illustrated in the Programmable CSRW construction 260, which is illustrated in FIG. 15, there is shown the construction process for the CSRW buffer 74 of the Wireless ECG monitoring device 10. The ECG device continuously saves the patient's recorded data both in the CSRW buffers 74, which overwrites itself after a given and programmable size, and in the received ECG data buffer 72 of the ECG monitoring device 10. In the event that abnormal cardiovascular activity is detected, the CSRW buffers 74 in the memory module 70 of the wireless ECG monitoring device will then be transmitted to a computing device 15 via the wireless transceivers 60 for further analysis. The outside computing device 15 then utilizes its superior processing power as well as its access to the patient's historical data, to generate additional software algorithms that are best fit for that patient. The new algorithms are then downloaded to the ECG device 10 and saved in the downloaded algorithm memory 78 using wireless transceivers 60 via telemetry.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A portable ECG monitoring system comprising:
   a. a plurality of electrodes for sensing ECG signals;
   b. a processor to process and digitize the ECG signals;
   c. a transceiver for wirelessly transmitting the processed ECG signals to outside computing devices;
   d. a memory further comprised of at least one module, said memory stores the processed ECG signals, stores one or more pre-programmed algorithm software for detecting abnormal cardiovascular activities, stores downloadable custom algorithm software received from outside wireless computing devices, and stores Sliding Reporting Windows (SRWs) comprising of logs of recently recorded ECG signals prior to and including each abnormal cardiovascular event, and
   e. wherein the ECG processor continuously performs analysis on the recorded cardiovascular activities using pre-loaded algorithms, the recorded data is stored in the memory and transmitted to outside computers via the ECG's transceivers, the detection of an abnormal event triggers an alarm, stores and logs the most recent history of patient's recorded data just prior to and including the abnormal event in its SRW buffer memory, and transmits the SRW data wirelessly to an outside computing device for further analysis whereby further additional complex algorithms on the recorded data are performed to determine the most suitable custom software algorithm which is then downloaded into the ECG downloadable algorithm memory wirelessly.

2. The monitoring system of claim 1, wherein the time duration of recorded data of said SRW buffer memory is adjusted via a series of commands from outside computing device using the wireless transceivers of the ECG device.

3. The monitoring system of claim 1, wherein the data recorded in said SRW buffer is uploaded into an outside computing device via software commands using the wireless transceivers of the ECG device.

4. The monitoring system of claim 1, wherein the data recorded in said SRW buffer is compressed using compression algorithms before transmission to an outside computing device, after which the outside computing device decompresses the received ECG data for further analysis and viewing by healthcare provider.

5. The monitoring system of claim 1, wherein the outside computing device sends the received SRW buffer to a remote computer server station connected to the Internet for further analysis and viewing by healthcare provider using a web-based service.

6. The monitoring system of claim 1, wherein any of the at least one pre-programmed detection algorithms is selected to analyze patient ECG data via software commands from outside computing device using the wireless transceivers of the ECG device.

7. The monitoring system of claim 1, wherein any of the said downloadable custom detection algorithms is selected to analyze patient ECG data, via software commands from outside computing device using the wireless transceivers of the ECG device.

8. A portable ECG monitoring system comprising:
   a. a plurality of electrodes for sensing ECG signals;
   b. a processor to process and digitize the ECG signals;
   c. a transceiver for wirelessly transmitting the processed ECG signals to outside computing devices;
   d. a memory further comprised of at least one module, said memory stores the processed ECG signals, stores one or more pre-programmed algorithm software for detecting abnormal cardiovascular activities, stores downloadable custom algorithm software received from outside wireless computing devices, and stores Circular Sliding Reporting Windows (CSRWs) comprising of logs of recently recorded ECG signals prior to and including each abnormal cardiovascular event, and
   e. wherein the ECG processor continuously performs analysis on the recorded cardiovascular activities using pre-loaded algorithms, the recorded data is simultaneously stored in both the ECG recorded signal memory as well as the CSRW buffer memory, the detection of an abnormal event triggers an alarm, creates a log of the current CSRW buffer, and transmits the CSRW data wirelessly to an outside computing device for further analysis whereby further additional complex algorithms on the recorded data are performed to determine the most suitable custom software algorithm which is then downloaded into the ECG downloadable algorithm memory wirelessly.

9. The monitoring system of claim 8, wherein the time duration of recorded data of said CSRW buffer memory can be adjusted via a series of commands from outside computing device using the wireless transceivers of the ECG device.

10. The monitoring system of claim 8, wherein the data recorded in said CSRW buffer is uploaded into an outside computing device via software commands using the wireless transceivers of the ECG device.

11. The monitoring system of claim 8, wherein the data recorded in said CSRW buffer is compressed using compression algorithms before transmission to an outside computing device, after which the outside computing device decompresses the received ECG data for further analysis and viewing by healthcare provider.

12. The monitoring system of claim 8, wherein the outside computing device sends the received CSRW buffer to a remote computer server station connected to the Internet for further analysis and viewing by healthcare provider using a web-based service.

13. The monitoring system of claim 8 wherein any of the at least one pre-loaded custom detection algorithms is selected to analyze patient ECG data via software commands from outside computing device using the wireless transceivers of the ECG device.

14. The monitoring system of claim 8, wherein any of the said custom downloaded algorithms can be activated to detect abnormal cardiovascular activities via a series of commands form an outside computing device.

15. An interactive process and method for detecting a patient's abnormal cardiovascular activities utilizing an ECG monitoring device and having at least one stored detection algorithm, comprising:
  a. selecting a detection algorithm that is residing in the memory of the ECG device;
  b. activating the most recently selected detection algorithm;
  c. recording ECG signals by an ECG monitoring device;
  d. processing the ECG signals;
  e. storing the processed ECG signals in the memory of the ECG device;
  f. analyzing the recorded ECG signals for abnormalities using the active algorithm;
  g. iteratively repeating steps a-f until an abnormal cardiovascular activity is detected;
  h. transmitting wirelessly to an outside computing device the most recent history of patient's recorded ECG signals prior to and including the abnormal cardiovascular event;
  i. utilizing the outside computing device to further analyze the transmitted ECG signals;
  j. determining a suitable custom software algorithm by the outside computing device for in-depth analysis of ECG signals that is appropriate for the patient's monitoring needs;
  k. downloading from the outside computing device to the ECG monitoring device the customized in-depth software algorithm as determined from step j;
  l. prompting of the ECG monitoring device by the outside computing device to select the custom algorithm that was downloaded in the previous step; and
  m. resuming the interactive process and method from step b.

16. The interactive process and method of claim 15, wherein the time duration of the most recent history of patient's recorded ECG signals prior to and including the abnormal cardiovascular event is adjusted via a series of commands from outside computing device using the wireless transceivers of the ECG device.

17. The interactive process and method of claim 15, wherein the most recent history of patient's recorded ECG signals prior to and including the abnormal cardiovascular event is compressed using compression algorithms before transmission to an outside computing device, after which the outside computing device decompresses the received ECG data for further analysis and viewing by healthcare provider.

18. The interactive process and method of claim 15, wherein the outside computing device sends the received most recent history of patient's recorded ECG signals prior to and including the abnormal cardiovascular event to a remote computer server station connected to the Internet for further analysis and viewing by healthcare provider using a web-based service.

19. The interactive process and method of claim 15, wherein any of the said preprogrammed and the said downloadable custom detection algorithms is selected to analyze patient ECG data, via software commands from outside computing device using the wireless transceivers of the ECG device.

20. The interactive process and method of claim 15, wherein the detection of an abnormal cardiovascular event further triggers an alarm on the ECG to alert the patient and surrounding persons and transmits an alert to the outside computing device which will then notify health care provider, designated persons and emergency care professionals as appropriate.

* * * * *